United States Patent [19]
Schiraldi et al.

[11] Patent Number: 5,910,613
[45] Date of Patent: Jun. 8, 1999

[54] METHOD OF PRODUCTION OF AROMATIC ALDEHYDES CATALYZED BY TRIFLIC ACID

[75] Inventors: David Anthony Schiraldi, Charlotte, N.C.; Jeffrey Charles Kenvin, Alpharetta, Ga.

[73] Assignee: HNA Holdings, Inc., Charlotte, N.C.

[21] Appl. No.: 09/073,290

[22] Filed: May 6, 1998

[51] Int. Cl.$^6$ .................................................. C07C 45/00
[52] U.S. Cl. ........................... 568/428; 568/420; 568/426
[58] Field of Search ..................................... 568/428, 426, 568/420

[56] References Cited

FOREIGN PATENT DOCUMENTS 51-146430  12/1976  Japan .

OTHER PUBLICATIONS

Brian L. Booth and Teymour A. El–Fekky, "A Comparison of the Effectiveness of Sulphiric Acid and Trifluoromethanesulphonic Acid in Koch Carboxylation Reactions", Journal of Chemical Society, 1979, pp. 2441–2447.

Brian L. Booth and Teymour A. El–Fekky, "Formylation and Acylation Reactions Catalysed by Trifluoromethanesulphonic Acid", Journal of Chemical Society, 1980, pp. 181–185.

George A. Olah, Khosrow Laali and Omar Farooq, "Superacid–Catalyzed Formylation of Aromatics with Carbon Monoxide", Journal of Organic Chemistry, vol. 50, 1985 pp. 1483–1486.

*Primary Examiner*—Shailendra Kumar
*Assistant Examiner*—S. Padmanabhan
*Attorney, Agent, or Firm*—Gregory N. Clements

[57] ABSTRACT

A process for producing aromatic aldehydes by carbonylation of an arene in the presence of triflic acid catalyst is described by reacting an arene, such as toluene, with carbon monoxide in the presence of triflic acid (as a catalyst), for a reaction time less than 90 minutes, at a carbon monoxide partial pressure of about 700–2000 psig, at a temperature of from about 0–50° C. to produce an aromatic aldehyde such as tolualdehyde and by-products, the by-products being less than 5% by weight based on the total reaction products.

The mole ratio of triflic acid to arene is between about 0.8 to 20, with the reaction having an isomer selectivity greater than 95% by weight for the para isomer aldehyde, and showing substantially no meta isomer.

24 Claims, 1 Drawing Sheet

METHOD OF PRODUCTION OF AROMATIC ALDEHYDES CATALYZED BY TRIFLIC ACID

FIELD OF THE INVENTION

The present invention relates to a process for producing aromatic aldehydes and in particular the carbonylation of an arene by using triflic acid as a catalyst. More specifically, the present invention concerns the method of carbonylation of toluene in the presence of a triflic acid catalyzed system to yield p-tolualdehyde. The particular catalyst system comprises triflic acid, otherwise known as trifluoromethane sulfonic acid. More particularly, the present invention comprises the reaction of an arene with carbon monoxide in the presence of triflic acid having a reaction time of less than 1½ hours and preferably less than 1 hour; at a carbon monoxide partial pressure of about 700 to about 2000 psig and preferably 900–1200 psig; to produce yields of aldehydes of about 14 to 99%, and preferably 70–99%, by weight having a selectivity of greater than 95%, and preferably greater than 98% by weight for the para substituted aldehyde, with less than 5% by-product (by-product being defined as a non-aldehyde composition).

PRIOR ART

Carbonylation of arenes is inherently interesting from a commercial point of view. Relatively few inexpensive and environmentally-friendly routes exist to add carbon atoms to aromatic feedstocks. Of special interest is the carbonylation of toluene to yield the para isomer of tolualdehyde (pTal). The pTal molecule can be readily oxidized to ultimately yield DMT (dimethyl terephthalate) and/or TA (terephthalic acid).

In the Journal of Chemical Society, Perkins Transactions I, 1979, pages 2441–2447 an article by Booth et al. disclosed the use of triflic acid as a catalyst for the carbonylation of olefins, alcohols, and esters. The major teaching of this paper is that triflic acid is generally superior to sulfuric acid in the carbonylation of aliphatic and cycloaliphatic substrates. No mention of aromatic substrates is made.

In another article in the Journal of the Chemical Society, Perkins Transactions I, 1980, pages 181–185 Booth et al. disclose their initial work to include carbonylations of aromatic substrates. Aromatic substrates described in this paper include but are not limited to benzene, toluene, p-xylene, m-xylene, and 1, 3,5-trimethyl benzene. Specific to toluene, the author has disclosed the following reaction conditions and results.

| Ratio Triflic Acid to Toluene | Temperature °C. | Pressure PSIG | Time - Hours | Product Yields |
|---|---|---|---|---|
| 1.0 | + 25° | 15 | 16 | 5% |
| 1.7 | + 25° | 1875 | 4 | 72% |

No other products other than p-Tal were detected in the two above examples.

In an article in the Journal of Organic Chemistry, Volume 50, 1985, pages 1483–1486, Olah, et al. disclose triflic acid catalyzed carbonylation of aromatic substrates. The aromatic substrates comprise several different arenes including toluene. Specific to toluene, the authors employing conditions similar to those of Booth et al. refute the selectivity numbers previously reported, i.e., the product yields include o-Tal and m-Tal. Additionally, the authors demonstrate a total tolualdehyde yield of 8–79% with a maximum tolualdehyde isomer selectivity to para of 92%, with yield to condensation by-products of approximately 18–20%. The examples of toluene carbonylation given by Olah et al are:

| Example | Ratio Triflic Acid to Toluene | Temperature °C. | Pressure PSIG | Time - Hours | Aldehydes Yield |
|---|---|---|---|---|---|
| I. | 0.25 | 25° | 1200 | 24 | 8% |
| II. | 1.0 | 25° | 1200 | 17 | 14% |
| III. | 1.0 | 65° | 1200 | 17 | 18% |
| IV. | 6.0 | 25° | 1200 | 3.5 | 79 |

Based upon the disclosure that the maximum para selectivity is 92% with the ortho and meta isomers formed being 5.6% and 2.6% respectively, the actual yields for Olah et al are:
I. 7.4% p-Tal/0.4% o-Tal/0.2% m-Tal+by-products
II. 12.8% p-Tal/0.8% o-Tal/0.4% m-Tal+by-products
III. 16.5% p-Tal/1.0% o-Tal/0.5% m-Tal+by-products
IV. 72.5% p-Tal/4.4% o-Tal/2.1% m-Tal+by-products In Japanese Laid-Open Patent Application 51-146430 to Suzuki et al. (assigned to Mitsubishi Kasei Corp.) dated Dec. 16, 1976 describe a method for manufacturing tolualdehyde by triflic acid catalyzed carbonylation of toluene. The examples of toluene carbonylation given by Suzuki:

| Ratio Triflic Acid to Toluene | Temperature °C. | Pressure PSIG | Time - Hours | Product Yield |
|---|---|---|---|---|
| 0.9 | 8° | 570 | 1.5 | 21% p-Tal/1.2% m-Tal |
| 0.9 | 17° | 570 | 1.5 | 13% p-Tal/0.95 m-Tal |
| 0.9 | 50° | 570 | 1.5 | 5% p-Tal/0.24 m-Tal |

Also disclosed in Suzuki are FIGS. 1 and 2 which report the relationship between carbon monoxide pressure to toluene for effective aldehyde yield, and the relationship between the ratio of triflic acid to toluene in yielding tolualdehyde. This data is not from the examples set forth therein. Assuming that the graphs report data produced while holding all other variables constant, these graphs suggest that toluene conversion increases with reaction pressure, and that conversion increases with higher triflic acid to toluene ratios. Suzuki fails to mention the ortho isomers, although Booth and Olah have demonstrated its presence in small amounts.

SUMMARY OF THE INVENTION

The present invention defines a solid set of reaction conditions which are novel that yield demonstratively superior results. Those reaction conditions are: 1) isomer selectivities greater than 95% by weight for the para isomer; 2) producing condensation by-products of less than 5%, and preferably less than 2%, and most preferably less than 0.1% by weight based on the total reaction products of aldehydes and by-products; 3) carbonylation reaction time that is less than 1½ hours, preferably less than 1 hour, and most preferably between 5–45 minutes; and 4) reaction product showing substantially no m-Tal isomer (less than 0.3% by weight). The process of the present invention is designed to include reaction pressures between 700–2000 psig, and preferably 900–1200 psig; with a mole ratio of triflic acid to arene between about 0.8 to 20, and preferably 6 to 12; with a reaction temperature between 0 and 50° C., preferably between 20 and 40° C.

The present invention comprises a process for reacting an arene (e.g. toluene) with carbon monoxide in the presence of triflic acid as a catalyst to yield aldehydes, the process comprising: 1) reacting the arene and the carbon monoxide in the presence of the triflic acid when the mole ratio of triflic acid to arene is from 0.8 to 20, where said reaction temperature is between 0–50° C., at a CO reaction partial pressure between about 700 and about 2000 psig at a reaction time of less than 1.5 hours.

The present invention also relates to a process comprising: reacting carbon monoxide with an arene to yield one or more aldehydes, for a reaction time of less than 1.5 hours, said reaction having a para isomer selectivity of greater than 95% by weight, and condensation by-products of less than 5% by weight.

THE DRAWING

The drawing is a graph of the selectivity for para isomer aldehyde vs. the acid ratio. The acid ratio is the ratio of the number of moles of triflic acid to the number of moles of arene.

DESCRIPTION OF THE PREFERRED EMBODIMENTS

Figure 1:
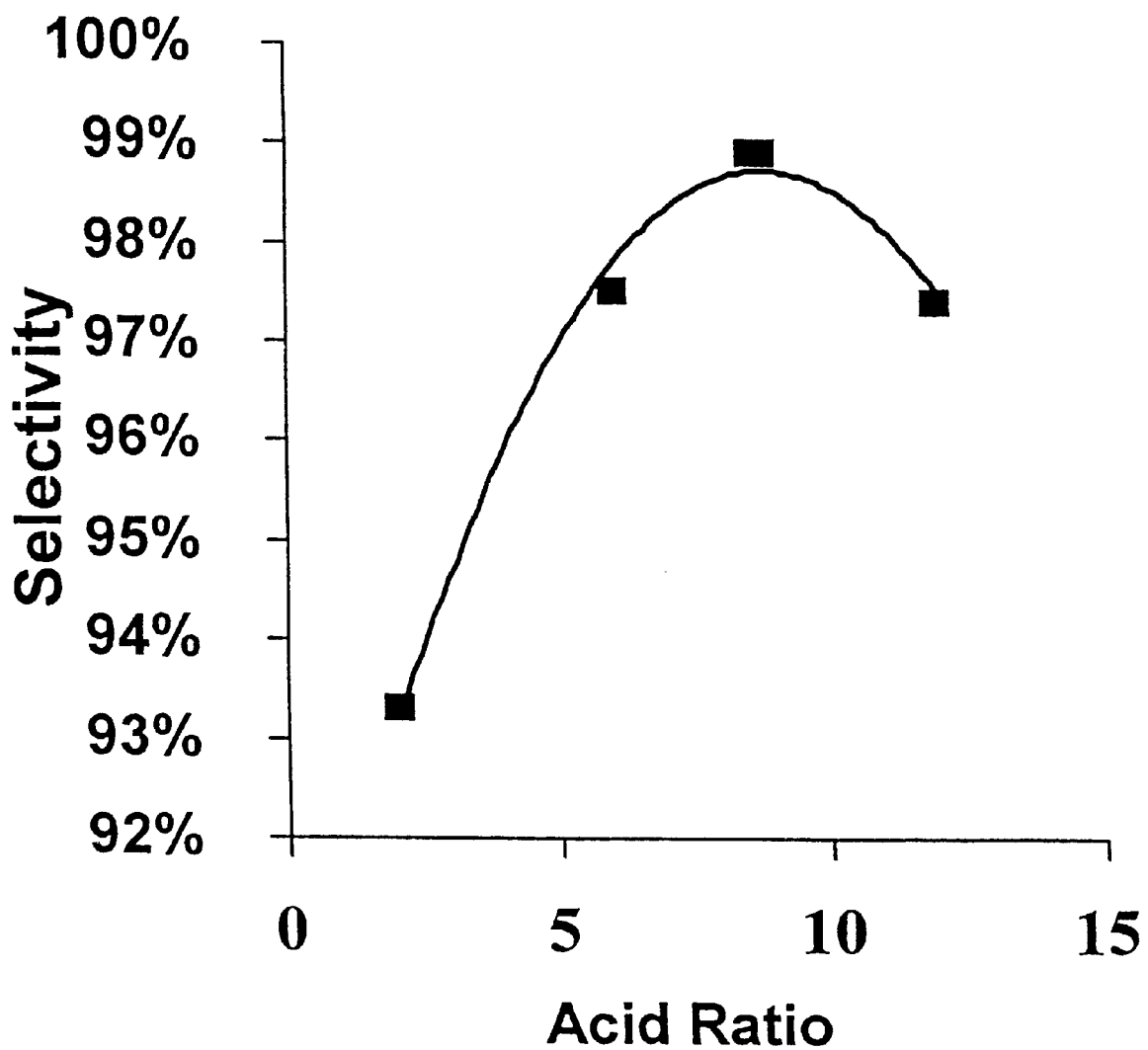

A simplistic reaction mechanism of arene with carbon monoxide in the presence of triflic acid as a catalyst to yield aldehyde is set forth below.

It is crucial that the triflic acid and the arene be essentially anhydrous since the presence of water will limit catalytic activity. In other words, a hydrated triflic acid has significantly reduced catalytic activity, and should the arene contain significant quantities of water, it is conceivable that it could or would hydrate the triflic acid such that little catalytic activity occurs.

A pressurized vessel is used for the reaction. An arene (such as toluene) and triflic acid are supplied after the vessel has been purged with nitrogen or other inert gas as needed. After the arene and triflic acid are added, the carbon monoxide is introduced into the system under agitation such that sufficient liquid-vapor contact occurs. Upon completion of the reaction, the unreacted carbon monoxide is removed by releasing the pressure, such as venting to the atmosphere or releasing the pressure in a manner to recover the carbon monoxide for later use. The reaction mixture is then mixed with water and the organic layer is separated and recovered by simple use of separatory funnel. The triflic acid remains in the water portion and is thus separated from the organic layer having the aldehyde therein. The triflic acid can easily be recovered from the water portion by a distillation process, for example, and recycled for use. The organic or hydrocarbon liquid layer can then be analyzed for aldehyde content by gas chromatography mass spectrometry procedures well known to those skilled in the art.

Suitable arene useful in the present invention are: toluene, styrene, cumene, ethylbenzene, benzene, xylene, and generally any benzene ring with one or more an organic aliphatic constituents depending therefrom.

The process of the present invention reacts carbon monoxide with an arene in the presence of triflic acid (acting as a catalyst). The reaction time is less than 1½ hours at a reaction pressure of 700–2000 psig. When the reaction time exceeds about 1½ hours no more significant amount of aldehyde is produced. Thus as a practical matter and an economical matter, less than 1½ hours is more desirable. When the reaction pressure is less than about 700 psig, the reaction time may exceed 1½ hours and becomes impractical. When the reaction pressure exceeds 2000 psig, operational costs and capitol equipment costs become impractical.

The amount of catalyst employed impacts the reaction. The desired reaction is the production of the para isomer aldehyde. The desired reaction has a selectivity for the para isomer aldehyde greater than 95% when the mole ratio of triflic acid to arene (called acid ratio) is between 0.8 to 20, and preferably 6–12. The drawing is a graph of para isomer tolualdehyde selectivity verses acid ratio (mole ratio of triflic acid to toluene). Thus, when the arene employed is toluene (thereby yielding tolualdehyde) the 95% by weight selectivity for para-toluadehyde occurs when the acid ratio is between about 4 and about 15 (extrapolation), with peak results occurring when the acid ratio is about 8.8. Other arenes give similar results when the acid ratio is between about 0.8 to about 20. Having an acid ratio below 0.8 generally does not give para isomer aldehyde selectivities of greater than 95% by weight. Having an acid ratio greater than 20 also generally does not yield para isomer aldehyde selectivities greater than 95%0 by weight and also the reaction costs become prohibitively expensive causing the resultant aldehyde to have virtually no commercial value.

When the reaction temperature is between 0 and 50° C. the desired product results (when all other conditions are met). Temperatures below 0 C. generally cause excessively long reaction times, whereas temperatures above about 50° C. are functional, but improved results do not occur, thus causing an increase in the process costs with no more desired product being produced.

The present invention is demonstrated by the following Examples and Comparative Examples.

EXAMPLE I

A mixture of trifluoromethanesulfonic acid (anhydrous, 21 grams, 140 mmole) and toluene (anhydrous, 6.8 grams, 74 mmole) was charged to a 50 ml capacity reactor. The reactor was sealed and then purged with inert gas (helium, nitrogen, or argon) to remove any air. The reactor was pressurized to 1100 psig(74.8 atm) of carbon monoxide (CO). The mixture was vigorously agitated for 5 minutes at 25° C.

The excess gas was vented and a reddish brown liquid was recovered from the reactor. The liquid product was slowly mixed with water (50 grams) and sodium bicarbonate (2 grams). The mixture was filtered to separate the solids from the liquid products. The filtered liquid was treated with diethyl ether (30 ml) to form two liquid phases—a hydrocarbon phase and an aqueous phase. The liquid phases were then separated using a separatory funnel.

The hydrocarbon liquid was analyzed by GCMS showing the following product compositions:

p-Tolualdehyde 19.33%
o-Tolualdehyde 0.46%
Toluene 80.21%
By-products not detected

EXAMPLE II

A mixture of trifluoromethanesulfonic acid (anhydrous, 23 grams, 153 mmole) and toluene (anhydrous, 9.2 grams, 100 mmole) were charged to a 50 ml capacity reactor. The reactor was sealed and then purged with inert gas (helium, nitrogen, or argon) to remove any air. The reactor was pressurized to 1100 psig (74.8 atm) with carbon monoxide (CO). The mixture was vigorously agitated for 15 minutes at 25° C.

The hydrocarbon liquid phase was recovered using the same procedure as used in Example I and was analyzed by GCMS and the tolualdehyde yields and selectivity are listed in Table I.

EXAMPLE III

A mixture of trifluoromethanesulfonic acid (anhydrous, 22.8 grams, 152 mmole) and toluene (anhydrous, 7.1 grams, 76 mmole) were charged to a 50 ml capacity reactor. The reactor was sealed and then purged with inert gas (helium, nitrogen, or argon) to remove any air. The reactor was pressurized to 1100 psig (74.8 atm) with carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed in Table I.

EXAMPLE IV

A mixture of trifluoromethanesulfonic acid (anhydrous, 36.11 grams, 241 mmole and toluene (anhydrous, 11.3 grams, 123 mmole) were charged to a 50 ml capacity reactor. The reactor was sealed and then purged with inert gas (helium, nitrogen, or argon) to remove any air. The reactor was pressurized to 1100 psig (74.8 atm) with carbon monoxide (CO). The mixture was vigorously agitated for 60 minutes at 25° C.

The hydrocarbon liquid phase was recovered using the same procedure as used in Example I and was analyzed by GCMS and the tolualdehyde yields and selectivity are listed in Table I.

COMPARATIVE EXAMPLE 1

A mixture of trifluoromethanesulfonic acid (anhydrous, 32.7 grams, 218 mmole and toluene (anhydrous, 10 grams, 108 mmole) was charged to a 50 ml capacity reactor. The reactor was sealed and then purged with inert gas (helium, nitrogen, or argon) to remove any air. The reactor was pressurized to 1100 psig (74.8 atm) with carbon monoxide (CO). The mixture was vigorously agitated for 1050 minutes at 25° C.

The hydrocarbon liquid phase was recovered using the same procedure as used in Example I and was analyzed by GCMS and the tolualdehyde yields and selectivity are listed in Table I.

COMPARATIVE EXAMPLE 2

A mixture of trifluoromethanesulfonic acid (anhydrous, 19.2 grams, 128 mmole and toluene (anhydrous, 12.8 grams, 139 mmole) were charged to 50 ml capacity reactor. The reactor was sealed then purged with inert gas (helium, nitrogen, or argon) to remove any air. The reactor was pressurized to 500 psig (34 atm) with carbon monoxide (CO). The mixture was vigorously agitated for 90 minutes at 25 C.

The hydrocarbon liquid phase was recovered using the same procedure as used in Example I and was analyzed by GCMS and the tolualdehyde yields and selectivity are listed in Table I.

EXAMPLE V

A mixture of trifluoromethanesulfonic acid (anhydrous 23.93 grams, 160 mmole) and toluene (anhydrous, 2.45 grams, 27 mmole) was charged to a 50 ml capacity reactor. The reactor was sealed and then purged with inert gas (helium, nitrogen, or argon) to remove any air. The reactor was pressurized to 2000 psig (136 atm) of carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed in Table I.

EXAMPLE VI

A mixture of trifluoromethanesulfonic acid (anhydrous, 22.6 grams, 151 mmole) and toluene (anhydrous, 2.31 grams, 25 mmole) was charged to a 50 ml capacity reactor. The reactor was sealed and then purged with inert gas (helium, nitrogen, or argon) to remove any air. The reactor was pressurized to 1100 psig (74.8 atm) of carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed in Table I.

EXAMPLE VII

A mixture of trifluoromethanesulfonic acid (anhydrous, 50 grams, 331 mmole) and toluene (anhydrous, 3.48 grams, 38 mmole) was charged to a 50 ml capacity reactor. The reactor was sealed and then purged with inert gas (helium, nitrogen, or argon) to remove any air. The reactor was pressurized to 1000 psig (68 atm) of carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed in Table I.

EXAMPLE VIII

A mixture of trifluoromethanesulfonic acid (anhydrous, 48.7 grams, 325 mmole) and toluene (anhydrous, 2.5 grams, 27 mmole) was charged to a 50 ml capacity reactor. The reactor was sealed and then purged with inert gas (helium, nitrogen, or argon) to remove any air. The reactor was pressurized to 1000 psig (68 atm) of carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed in Table I.

EXAMPLE IX

A mixture of trifluoromethanesulfonic acid (anhydrous, 48.9 grams, 326 mmole) and toluene (anhydrous, 2.07 grams, 22.5 mmole) was charged to a 50 ml capacity reactor. The reactor was sealed and then purged with inert gas (helium, nitrogen, or argon) to remove any air. The reactor was pressurized to 1000 psig (68 atm) of carbon monoxide (CO). The mixture was vigorously agitated for 15 minutes at 25° C.

The hydrocarbon liquid phase was recovered using the same procedure as used in Example I and was analyzed by GCMS and the tolualdehyde yields and selectivity are listed in Table I.

EXAMPLE X

A mixture of trifluoromethanesulfonic acid (anhydrous, 49.4 grams, 329 mmole) and toluene (anhydrous, 2.05 grams, 22.25 mmole) was charged to a 50 ml capacity reactor. The reactor was sealed and then purged with inert gas (helium, nitrogen, or argon) to remove any air. The reactor was pressurized to 1000 psig (68 atm) of carbon monoxide (CO). The mixture was vigorously agitated for 60 minutes at 25° C.

The hydrocarbon liquid phase was recovered using the same procedure as used in Example I and was analyzed by GCMS and the tolualdehyde yields and selectivity are listed in Table I.

EXAMPLE XI

A mixture of trifluoromethanesulfonic acid (anhydrous, 49.4 grams, 329 mmole) and toluene (anhydrous, 2.05 grams, 22.25 mmole) was charged to a 50 ml capacity reactor. The reactor was sealed and then purged with inert gas (helium, nitrogen, or argon) to remove any air. The reactor was pressurized to 1600 psig (109 atm) of carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed in Table I.

EXAMPLE XII

A mixture of trifluoromethanesulfonic acid (anhydrous, 49.7 grams, 331 mmole) and toluene (anhydrous, 3.57 grams, 38.75 mmole) was charged to a 50 ml capacity reactor. The reactor was sealed and then purged with inert gas (helium, nitrogen, or argon) to remove any air. The reactor was pressurized to 1000 psig (68 atm) of carbon monoxide (CO). The mixture was vigorously agitated for 30 minutes at 25° C.

The hydrocarbon liquid phase was recovered using the same procedure as used in Example I and was analyzed by GCMS and the tolualdehyde yields and selectivity are listed 4n Table I.

Thus it is apparent that there has been provided, in accordance with the invention, a process that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

What is claimed is:

1. A process for the production of aldehyde by carbonylation of an arene using triflic acid comprising:

reacting an arene with carbon monoxide in the presence of triflic acid for a reaction time of less than 1.5 hours, at a carbon monoxide partial pressure ranging from about 700 to about 2000 psig, and at a temperature between 0 and 50° C., produce aromatic aldehydes and by-products.

2. The process of claim 1, wherein the mole ratio of triflic acid to arene is from 0.8 to 20.

3. The process of claim 1, wherein said arene is selected from the group consisting of benzene, styrene, xylene, ethylbenzene, cumene, and toluene.

4. The process of claim 3, wherein said arene is toluene.

5. The process of claim 4, wherein said aromatic aldehydes are tolualdehydes having an isomer selectivity greater than 95% by weight for the para isomer.

6. The process of claim 5, wherein said by-products are less than 5% by weight.

7. The process of claim 1, wherein said reaction time is less than about one hour.

8. The process of claim 1, wherein said reaction time is be n about 5 to about 45 minutes.

9. The process of claim 1, wherein said mole ratio of triflic acid to arene is between about 6 to 12.

10. The process of claim 1, wherein said temperature is between about 20 and 40° C.

11. A process for the production of aldehyde by carbonylation in the presence of triflic acid comprising:

TABLE I

Triflic Acid Catalyzed Carbonylation of Toluene to p-Tolualdehyde

| Example | Acid Mole Ratio | Time, min | Pressure, psig CO | Temperature, °C. | Yield p-aldehyde by weight | Yield o-aldehyde by weight % | Yield by-products by weight % | Selectivity to p-aldehyde by weight |
|---|---|---|---|---|---|---|---|---|
| I | 1.9 | 5 | 1100 | 25 | 19.3% | 0.5% | — | 97.7% |
| II | 1.5 | 15 | 1100 | 25 | 14.3% | 0.3% | — | 98.3% |
| III | 2.0 | 30 | 1100 | 25 | 32.8% | 0.6% | 1.8% | 93.3% |
| IV | 2.0 | 60 | 1100 | 25 | 38.2% | 0.7% | 2.2% | 92.9% |
| Comp. Ex 1 | 2.0 | 1050 | 1100 | 25 | 26.7% | 0.6% | 52.0% | 33.7% |
| Comp. Ex 2 | 0.9 | 90 | 500 | 25 | 5.0% | 0.4% | 8.8% | 35.3% |
| V | 5.9 | 30 | 2000 | 25 | 76.5% | 0.2% | — | 99.7% |
| VI | 6.0 | 30 | 1100 | 25 | 49.0% | 0.8% | 0.5% | 97.5% |
| VII | 8.8 | 30 | 1000 | 25 | 98.9% | 0.7% | 0.4% | 98.9% |
| VIII | 12.0 | 30 | 1000 | 25 | 97.4% | 1.9% | 0.7% | 97.4% |
| IX | 14.5 | 15 | 1000 | 25 | 99.1% | 0.7% | 0.2% | 99.1% |
| X | 14.8 | 60 | 1000 | 25 | 98.9% | 0.5% | 0.6% | 98.9% |
| XI | 14.8 | 30 | 1600 | 25 | 99.6% | 0.2% | 0.2% | 99.6% |
| XII | 8.6 | 30 | 1000 | 25 | 98.9% | 0.7% | 0.5% | 98.9% | reacting an arene with carbon monoxide in the presence of triflic acid for a reaction time of less than 1.5 hours, at a carbon monoxide partial pressure of from about 700 to about 2000 psig, wherein the mole ratio of said triflic arene is from 0.8 to 20, to produce aldehyde having an isomer selectivity greater than 95% by weight for the para isomer aldehyde, and by-products, said by-products being less than 5% by weight based on the total reaction products.

12. The process of claim 11, wherein said arene is selected from the group consisting of benzene, styrene, xylene, ethylbenzene, cumene, and toluene.

13. The process of claim 12, wherein said arene is toluene.

14. The process of claim 13, wherein said mole ratio is 6 to 12.

15. The process of claim 14, wherein said mole ratio is about 8.8.

16. The process of claim 13, wherein said by-products are less than 2% by weight.

17. The process of claim 13, wherein said reaction time is less than one hour.

18. The process of claim 17, wherein said reaction time is less than about 45 minutes.

19. The process of claim 13, wherein said carbon monoxide partial pressure is between 1000–1100 psig.

20. The process of claim 11, wherein the reaction temperature is between 0 and 50° C.

21. The process of claim 17 wherein the mole ratio of triflic acid to toluene is between about 4 and about 15.

22. The process of claim 4 wherein the mole ratio of triflic acid to toluene is between about 4 and about 15.

23. The process of claim 22 wherein the carbon monoxide partial pressure is 900 to 1200 psig.

24. The process of claim 1 wherein the mole ratio of triflic acid to arene is 6 to 12, the carbon monoxide partial pressure is 900 to 1200 psig and the reaction time is less than one hour.

* * * * *